(12) United States Patent
Glode et al.

(10) Patent No.: US 8,983,637 B2
(45) Date of Patent: Mar. 17, 2015

(54) DETERMINING AUTHENTICITY OF REPORTED FITNESS-RELATED ACTIVITIES

(75) Inventors: Christopher M. Glode, Denver, CO (US); Robin J. Thurston, Austin, TX (US); Stewart Blanford, Littleton, CO (US)

(73) Assignee: MapMyFitness, Inc., Austin, TX (US)

( * ) Notice: Subject to any disclaimer, the term of this patent is extended or adjusted under 35 U.S.C. 154(b) by 0 days.

(21) Appl. No.: 13/561,107

(22) Filed: Jul. 30, 2012

(65) Prior Publication Data

US 2014/0031959 A1      Jan. 30, 2014

(51) Int. Cl.
*G06F 19/00*      (2011.01)

(52) U.S. Cl.
USPC ........................................................ 700/91

(58) Field of Classification Search
None
See application file for complete search history.

(56) References Cited

U.S. PATENT DOCUMENTS

| | | | |
|---|---|---|---|
| 7,080,065 B1 | 7/2006 | Kothuri et al. | |
| 7,092,846 B2 * | 8/2006 | Vock et al. | 702/182 |
| 7,881,902 B1 | 2/2011 | Kahn et al. | |
| 7,901,292 B1 | 3/2011 | Uhlir et al. | |
| 8,060,337 B2 | 11/2011 | Kulach et al. | |
| 8,112,251 B2 | 2/2012 | Case, Jr. et al. | |
| 8,364,389 B2 * | 1/2013 | Dorogusker et al. | 701/300 |
| 8,374,888 B2 * | 2/2013 | Earles et al. | 705/2 |
| 8,438,038 B2 * | 5/2013 | Cosentino et al. | 705/2 |
| 8,446,275 B2 * | 5/2013 | Utter, II | 340/539.12 |
| 2002/0040601 A1 | 4/2002 | Fyfe et al. | |
| 2005/0288154 A1 | 12/2005 | Lee et al. | |
| 2007/0021979 A1 * | 1/2007 | Cosentino et al. | 705/2 |
| 2007/0062279 A1 | 3/2007 | Chan et al. | |
| 2007/0208544 A1 | 9/2007 | Kulach et al. | |
| 2008/0096726 A1 | 4/2008 | Riley et al. | |
| 2009/0023555 A1 | 1/2009 | Raymond | |
| 2009/0076903 A1 * | 3/2009 | Schwarzberg et al. | 705/14 |
| 2009/0088962 A1 | 4/2009 | Jones | |
| 2009/0150178 A1 * | 6/2009 | Sutton et al. | 705/2 |
| 2009/0204597 A1 | 8/2009 | Mani et al. | |
| 2011/0032105 A1 | 2/2011 | Hoffman et al. | |
| 2011/0197157 A1 | 8/2011 | Hoffman et al. | |
| 2011/0289443 A1 | 11/2011 | Heaven et al. | |
| 2012/0028761 A1 | 2/2012 | Dorogusker et al. | |
| 2012/0116550 A1 | 5/2012 | Hoffman et al. | |
| 2012/0239173 A1 | 9/2012 | Laikari et al. | |

(Continued)

OTHER PUBLICATIONS

Neil Zhao, "Full-Featured Pedometer Design Realized with 3-Axis Digital Accelerometer," Analog Dialogue 44-06, Jun. (2010), 5 pages.

(Continued)

*Primary Examiner* — Seng H Lim
(74) *Attorney, Agent, or Firm* — Sprinkle IP Law Group

(57) ABSTRACT

An activity tracking system is configured to receive an activity report identifying a fitness-related action that is reported to have been completed by a participant. Upon receipt of the activity report, the activity reporting system verifies the workout, e.g., by obtaining data that can be used by the activity reporting system to determine whether the activity report represents actual activity as reported by the participant or, in the alternative, suspect activity. Based on the data obtained from the one or more data sources and the information in the activity report, the activity tracking system determines a probability that the activity report represents legitimate fitness activity. This probability determination may then be output or reported to other systems (e.g., fitness history databases, websites, and the like, third party systems (e.g., incentive systems, reward systems, and the like).

20 Claims, 4 Drawing Sheets

(56) References Cited

U.S. PATENT DOCUMENTS

| | | | |
|---|---|---|---|
| 2012/0253234 A1 | 10/2012 | Yang et al. | |
| 2012/0253488 A1 | 10/2012 | Shaw et al. | |
| 2012/0254212 A1 | 10/2012 | Shaw et al. | |
| 2012/0254226 A1 | 10/2012 | Shaw et al. | |
| 2013/0090749 A1* | 4/2013 | Oswald et al. | 700/91 |
| 2013/0158686 A1* | 6/2013 | Zhang et al. | 700/91 |
| 2014/0122494 A1 | 5/2014 | Thurston et al. | |
| 2014/0156215 A1 | 6/2014 | Eastman et al. | |

OTHER PUBLICATIONS

Eriksson, Martin et al., "Wireless Vertical Displacement Measurement During Running Using an Accelerometer and a Mobile Phone," Portuguese Journal of Sports Sciences 11 (suppl. 2), 2011, pp. 863-866, Porto, Portugal.

Bergamini, E., et al., "Estimation of Temporal Parameters During Sprint Running Using a Trunk-Mounted Inertial Measurement Unit," Journal of Biomechanical (2012), 4 pgs.

"What are Segments?" [Retrieved on Oct. 15, 2013 from <<https://strava.zendesk.com/entries/20945952-what-are-segments>>, 1 pg.].

"Segments—A New Tool for Analysis and Competition" [Retrieved on Oct. 15, 2013 from <<http://ridewithgps.com/segments/help>>, 12 pgs.].

International Search Report and the Written Opinion issued for PCT Application No. PCT/US2013/067834, mailed Mar. 28, 2014, 8 pgs.

International Search Report and the Written Opinion issued for PCT Application No. PCT/US2013/073178, mailed May 16, 2014, 8 pgs.

Office Action for U.S. Appl. No. 13/440,799, mailed May 4, 2012, 23 pgs.

Office Action for U.S. Appl. No. 13/077,410, mailed Jun. 11, 2012, 23 pgs.

Amendment for U.S. Appl. No. 13/440,799, dated Jul. 26, 2012, 8 pgs.

Amendment for U.S. Appl. No. 13/0770,410, dated Aug. 29, 2012, 8 pgs.

Office Action for U.S. Appl. No. 13/440,799, mailed Dec. 4, 2012, 29 pgs.

Office Action for U.S. Appl. No. 13/077,410, mailed Dec. 6, 2012, 31 pgs.

Veltkamp, Remco C., Shape Matching: Similarity Measures and Algorithms, Jan. 2001, No. UU-CS-2001-03, 16 pgs., Utrecht University, Utrecht, The Netherlands.

Chapman, Robert F. et al., Ground Contact Time as an Indicator of Metabolic Cost in Elite Distance Runners, Medicine & Science in Sports & Exercise, May 2012, vol. 44, pp. 917-925, Journal of the American College of Sports Medicine, Indianapolis, IN (http://www.acsm.org).

Snyder, Kristine L. et al., Energetically optimal stride frequency in running: the effects of incline and decline, The Journal of Experimental Biology 214, pp. 2089-2095, published Jun. 2011, The Company of Biologists Limited, Cambridge, UK.

Milner, Clare E. et al., Biomechical Factors Associated with Tibial Stress Fracture in Female Runners, Medicine & Science in Sports & Exercise, 2006, vol. 38, pp. 323-328, Journal of the American College of Sports Medicine, Indianapolis, IN (http://www.acsm.org).

\* cited by examiner

US 8,983,637 B2

DETERMINING AUTHENTICITY OF REPORTED FITNESS-RELATED ACTIVITIES

BACKGROUND

1. Technical Field

This disclosure relates generally to fitness-based activity tracking systems and, in particular, to methods and systems to determine the likelihood that a fitness-related or other reported activity was actually completed by a participant.

2. Background of the Related Art

Runners, cyclists, walkers, and other fitness enthusiasts today have access to numerous social wellness-oriented websites and associated mobile and tablet applications that permit them to track and store in an online database their daily running, cycling, walking or hiking routes. These sites may also provide useful community-based fitness content, searchable databases of events and courses, online training tools and fitness calculators. Mobile apps use the built-in GPS technology of the iPhone®, Android™, Windows® and Blackberry® mobile devices to enable users to record and chart their daily fitness activities and routes right on their devices. In particular, such mobile applications enable the user to record work-out details including, for example, duration, distance, pace, speed, elevation, calories burned, and route traveled on an interactive map. This workout data can then be saved to the website, where the user and others can view the data, build a comprehensive workout history, and the like.

In addition to mobile applications, other known devices (such as pedometers) measure and record physical activity, such as a number of steps taken.

While these physical activity recording devices work well for their intended purpose, some users may report amounts of activity using such devices that may not be consistent with the user's true level of physical activity. Indeed, recently a Company used pedometers to record the activities of employees as part of a Company challenge aimed at motivating employees to become more active in the workplace. Via their pedometer, some employees reported extraordinary large amounts of activity that were believed to be inconsistent with actual activity. When confronted, the employees admitted to cheating, e.g., by attaching the pedometer to a pet, putting the device in a cycling machine or fan, or other creative but necessarily deceptive actions.

The techniques described herein address this problem.

BRIEF SUMMARY

According to this disclosure, an activity tracking system is configured to receive an activity report identifying a fitness-related action that is reported to have been completed by a participant. Typically, the activity report represents a fitness workout. The activity report may be received from a source, such as the participant, or a device associated with the participant and that may be used to record and report data associated with the activity. Upon receipt of the activity report, the activity reporting system can verify the workout by obtaining data from one or more data sources and that can be used by the activity reporting system to determine whether the activity report represents actual activity as reported by the participant or, in the alternative, suspect activity, i.e., falsified activity data (in whole or in part). As described herein, the process of determining whether a workout represents true fitness activity is sometimes referred to as a "verified workout." Based on the data obtained from the one or more data sources and the information in the activity report, the activity tracking system determines a probability that the activity report represents legitimate fitness activity. This probability determination may then be output or reported to other systems (e.g., fitness history databases, websites, and the like, third party systems (e.g., incentive systems, reward systems, and the like).

The particular data used by the activity tracking system to determine whether reported activity data represents true fitness activity may be quite varied; typically, the data includes one or more of the following: the participant's history (e.g., one or more prior activity reports) or profile (e.g., the participant's height, weight, gender, age, or the like), as well as any available time-series tracks available for the participant, any available information about the source (e.g., the device) that provides the activity report, aggregate information about participants or devices that may be or are similar to the report (e.g., other participants with a similar profile had similar activity reports) including any type of time-series tracks available for similar participants or activity reports, and other reference data about the activity. Using this data, a permitted or authorized user or entity can verify a workout that is associated with or evidenced by the activity report.

The foregoing has outlined some of the more pertinent features of the subject matter. These features should be construed to be merely illustrative.

BRIEF DESCRIPTION OF THE DRAWINGS

For a more complete understanding of the present invention and the advantages thereof, reference is now made to the following descriptions taken in conjunction with the accompanying drawings, in which.

DETAILED DESCRIPTION OF AN ILLUSTRATIVE EMBODIMENT

Figure 1:
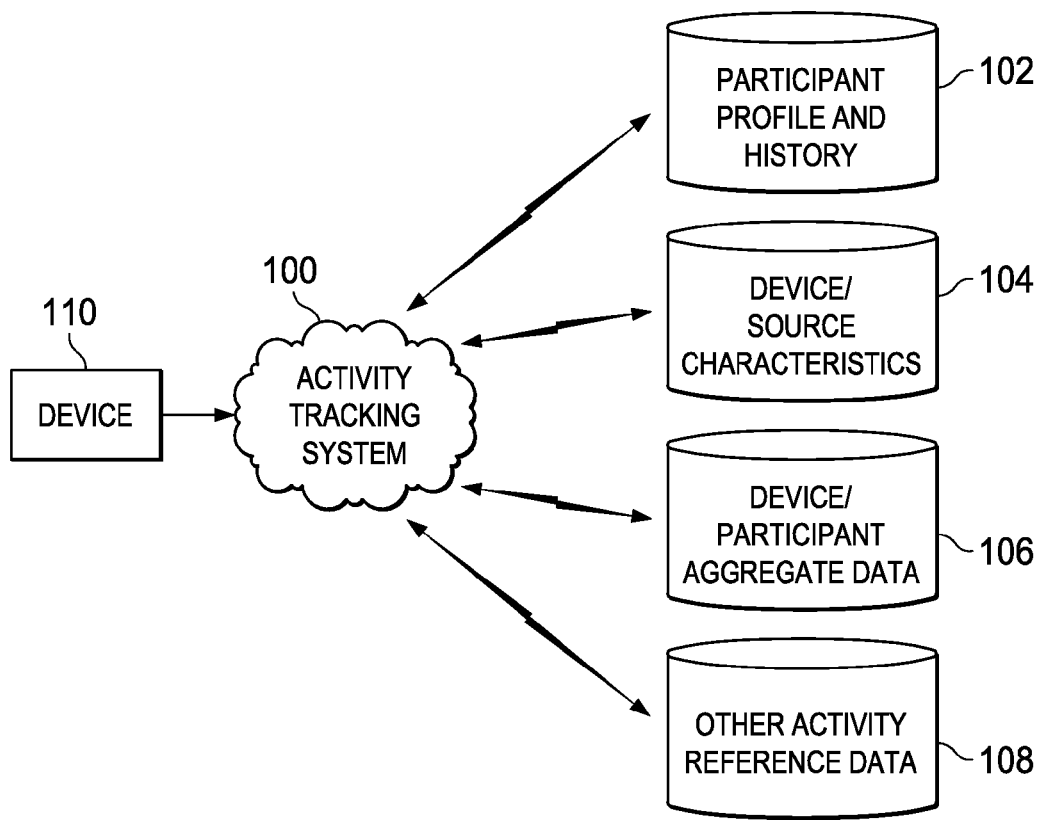
FIG. 1 is an exemplary activity tracking system in which the subject matter herein may be implemented.

As used herein, the following terms are defined as follows:

A "participant" is an entity, typically a person, for an activity is being reported. In this context, the participant usually is reported to have completed the activity.

An "activity" is an action that is reported to have been completed by a participant. An activity can be of varied scope, such as a type of exercise (e.g., biking, jogging, swimming, etc.) having a duration, a distance, a route, and/or other data related to that activity. Each such data may be considered an "attribute" of that activity. An activity attribute may also define other related information such as, without limitation, a food or meal that was reported to have been eaten by the participant in association with the activity, a weight or other bio-measurement (e.g., heart rate BPM, glucose level, or the like) that was reported to the participant at a given time before, during or after the activity, a period or pattern of sleep associated in some manner with the activity, a medicine or other medicament that was reported to have been administered by or to the participant in association in some way with the activity, and a course of exercise that was reported to have been completed by the participant. Thus, an activity has one or more such activity attributes and their associated values.

A "device" records, measures and/or reports activities. A device may be quite varied and include, without limitation, a pedometer that records the activity (e.g., steps taken) by the participant, a GPS-based watch or the like that records the physical location of the participant over time, a biometric device such as a weight scale or heart rate monitor that measures biometric information about the participant (e.g., as an individual reading, a series of individual readings over time, or a continuous stream of readings) during an activity, a piece of clothing (or footwear) with built-in sensors to capture data relating to an activity, or a mobile device that may record an activity using on-board sensors (i.e., GPS, accelerometer) or that may record them from other sensors nearby (e.g., a heart rate monitor that connects to the mobile device over a wireless link). Regardless of type, preferably each device may have different characteristics in terms of reporting frequency and capability, as well as expected and reported accuracy, and these characteristics typically should be considered when assessing the likely authenticity of an activity recorded or measured by the device. A device is one "source" of a reported activity.

A "source" is an originator of a report of an activity. The source of the report may be a participant, a device, or an entity. The entity may be an application or system (e.g., machine, program, process, or the like), an organization, a human entity, or a non-human entity. As will be seen, the source of the activity reported may provide significant value is assessing the likely authenticity of the report. Some non-limiting examples of sources of a reported activity thus may include: a device (e.g., a sleep sensor that reports a sleep pattern for a given time period), a participant who might self-report that a given food was eaten or a given action taken, an observer who might report or validate the activity, an application or system that may be a third party machine-based entity that may report that an activity was undertaken or completed, or some other third party (e.g., another human or non-human entity) that may report that a participant completed an activity. An example of the latter type might be a physical trainer that reports a heart rate measurement that was obtained during a workout session.

A "time-series track" is a sequence of measurements over time. A time series track may be intra-activity, or inter-activity. For example, an activity report that describes the heart rate of the participant during the activity may be an intra-activity time-series; or, a series of weight measurements, when taken over an extended period, may be an inter-activity time-series track.

An "activity report" is information or data associated with an activity. The activity report may include the identity of the activity, the participant, one or more devices, one or more sources, one or more time-series tracks, attributes and their values, and the like.

A "verified workout" is a fitness routine described by an activity report and that has a probability value indicative that the activity defined in the report actually occurred.

Referring now to FIG. 1, the subject matter herein operates in the context of an activity tracking system 100 having an associated set of databases 102, 104, 106 and 108. Database 102 includes data concerning participants and their history. Each participant may have a profile associated therewith. Database 104 includes data concerning devices and sources. Database 106 includes aggregate data, typically about other participants and/or devices that use the activity tracking system, although preferably the aggregate data does not necessarily disclose particular details about an individual participant. Database 108 includes other activity reference data. One or more of these databases may be integrated, and/or remote from one another and the activity tracking system. The databases may be third party or partner systems. Devices 110 interact with the activity tracking system over a network. The network depends on the nature of the device and the communication.

The activity tracking system 100 typically comprises machines, systems, sub-systems, applications, databases, interfaces and other computing and telecommunications resources. In one embodiment, the activity tracking system is implemented in an Internet-accessible platform operated by a service provider. Without limitation, the platform of this type comprises an Internet Protocol (IP) switch, a set of one or more web server machines, a set of one more application server machines, a database management system, and a set of one or more administrative or management server machines. A representative web server machine comprises commodity hardware (e.g., Intel-based), an operating system such as Linux, and a web server such as Apache 2.x. A representative application server machine comprises commodity hardware, Linux, and an application server such as Tomcat, JBoss, WebLogic, or the like. The database management system may be implemented as an Oracle (or equivalent) database management package running on Linux. In a high volume environment, there may be several web server machines, several application server machines, and a number of administrative and management server machines. Although not shown in detail, the infrastructure may include a name service, FTP servers, MRCP (Media Resource Control Protocol) servers, load balancing appliances, other switches, and the like. Each machine typically comprises sufficient disk and memory, as well as input and output devices. The software environment on each machine includes a Java virtual machine (JVM) if control programs are written in Java. Generally, the web servers handle incoming web-based requests and responses, providing web pages and content via known protocols and technologies. The application servers manage the basic functions of the activity tracking system that are described in more detail below.

One or more functions may be implemented in a cloud-based architecture. As is well-known, cloud computing is a model of service delivery for enabling on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. Available services models that may be leveraged in whole or in part include: Software as a Service (SaaS) (the provider's applications running on cloud infrastructure); Platform as a service (PaaS) (the customer deploys applications that may be created using provider tools onto the cloud infrastructure); Infrastructure as a Service (IaaS) (customer provisions its own processing, storage, networks and other computing resources and can deploy and run operating systems and applications).

The activity tracking system platform may comprise co-located hardware and software resources, or resources that are physically, logically, virtually and/or geographically distinct. Communication networks used to communicate to and from the platform services may be packet-based, non-packet based, and secure or non-secure, or some combination thereof.

Figure 2:
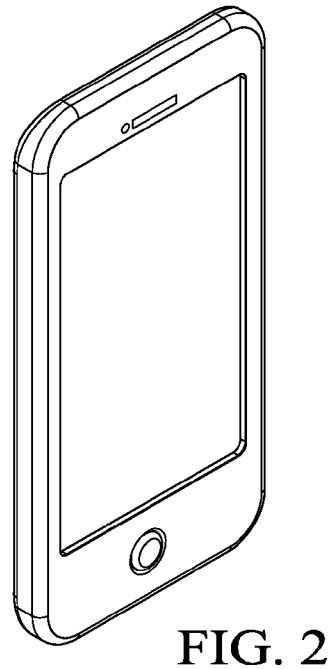
FIG. 2 is a representative mobile device that may be used to interact with the activity tracking system.
Figure 3:
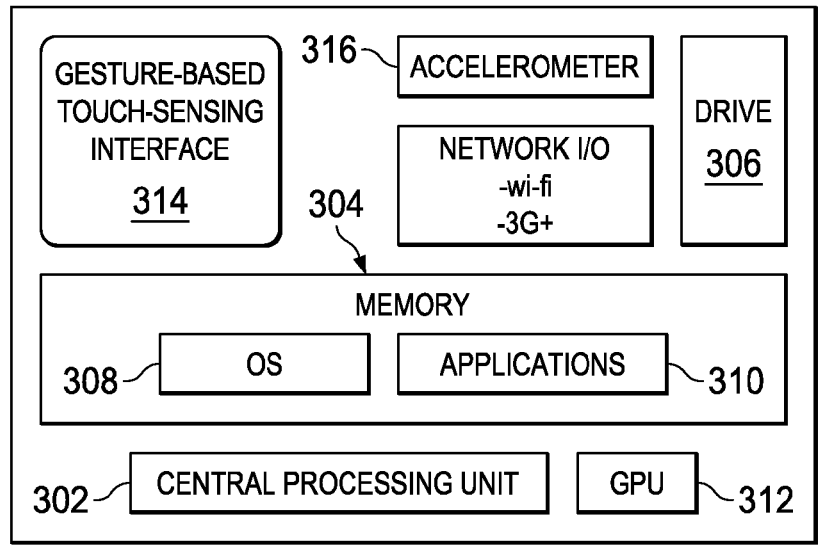
FIG. 3 illustrates representative hardware elements of the mobile device.

FIG. 2 illustrates a representative mobile device 200 that may be used to communicate with the activity tracking system platform. In a non-limiting embodiment, the mobile device is a smartphone or tablet, such as the iPhone® or iPad®, an Android™-based mobile device, or the like. As seen in FIG. 3, the device 300 comprises a CPU (central processing unit) 302, such as any Intel- or AMD-based chip, computer memory 304, such as RAM, and a drive 306. The device software includes an operating system (e.g., Apple iOS, Google® Android, or the like) 308, and generic support applications and utilities 310. The device may also include a graphics processing unit (GPU) 312. In particular, the mobile device also includes a touch-sensing device or interface 314 configured to receive input from a user's touch and to send this information to processor 312. The touch-sensing device typically is a touch screen. The touch-sensing device or interface 314 recognizes touches, as well as the position, motion and magnitude of touches on a touch sensitive surface (gestures). In operation, the touch-sensing device detects and reports the touches to the processor 312, which then interpret the touches in accordance with its programming. Typically, the touch screen is positioned over or in front of a display screen, integrated with a display device, or it can be a separate component, such as a touch pad. The touch-sensing device is based on sensing technologies including, without limitation, capacitive sensing, resistive sensing, surface acoustic wave sensing, pressure sensing, optical sensing, and/or the like. The touch-sensing can be based on single point sensing or multipoint sensing. Single point sensing is capable of only distinguishing a single touch, while multipoint sensing is capable of distinguishing multiple touches that occur at the same time. The touch-sensing can include actual contact of the touch-sensing device, near-touch of the touch-sensing device (e.g. detecting hovering), or remote detection of the user by the touch-sensing device.

The mobile device comprises suitable programming to facilitate gesture-based control, in a manner that is known in the art.

Generalizing, the mobile device is any wireless client device, e.g., a cellphone, pager, pedometer, GPS-based watch, scale, monitor, a personal digital assistant (PDA, e.g., with GPRS NIC), a mobile computer with a smartphone client, or the like. Other mobile devices in which the technique may be practiced include any access protocol-enabled device (e.g., a Blackberry® device, an Android™-based device, or the like) that is capable of sending and receiving data in a wireless manner using a wireless protocol. Typical wireless protocols are: WiFi, GSM/GPRS, CDMA or WiMax. These protocols implement the ISO/OSI Physical and Data Link layers (Layers 1 & 2) upon which a traditional networking stack is built, complete with IP, TCP, SSL/TLS and HTTP.

In a representative embodiment, the mobile device is a cellular telephone that operates over GPRS (General Packet Radio Service), which is a data technology for GSM networks. In addition to a conventional voice communication, a given mobile device can communicate with another such device via many different types of message transfer techniques, including SMS (short message service), enhanced SMS (EMS), multi-media message (MMS), email, WAP, paging, or other known or later-developed wireless data formats. Generalizing, a mobile device as used herein is a 3G- (or next generation) compliant device that includes a subscriber identity module (SIM), which is a smart card that carries subscriber-specific information, mobile equipment (e.g., radio and associated signal processing devices), a man-machine interface (MMI), and one or more interfaces to external devices (e.g., computers, PDAs, and the like). The techniques disclosed herein are not limited for use with a mobile device that uses a particular access protocol. The mobile device typically also has support for wireless local area network (WLAN) technologies, such as Wi-Fi. WLAN is based on IEEE 802.11 standards.

The mobile device preferably includes a 3-axis accelerometer 316 that measures acceleration. Signals output from the accelerometer 316 indicate the orientation of the device, typically relative to fixed platform, such as the earth's surface. The mobile device may also include a gyro (not shown), which measures rate of rotation around a particular axis.

A device as described herein preferably is configured or provisioned with an application (e.g., a mobile app) that performs one or more interactions with the activity tracking system. Of course, the nature and type of application will depend on the device. The application may be integral to the device or otherwise downloaded and installed in the device (e.g., as a plug-in, a software agent, a browser agent, a web app, a proprietary app, or the like). The activity tracking system also is configured or provisioned to perform one or more interactions with the databases or other external systems. These interactions may be over application programming interfaces (APIs) or via standard request-response protocols. Communications may be over secure connections. As a result of these interactions, a probability that an activity report is authentic (i.e., represents real data associated with the activity, as opposed to fabricated or other un-verifiable data) is generated. This enables the system or system provider to verify that a workout has in fact taken place.

These interactions are now described.

Determining Authenticity of Reported Activities

Figure 4:
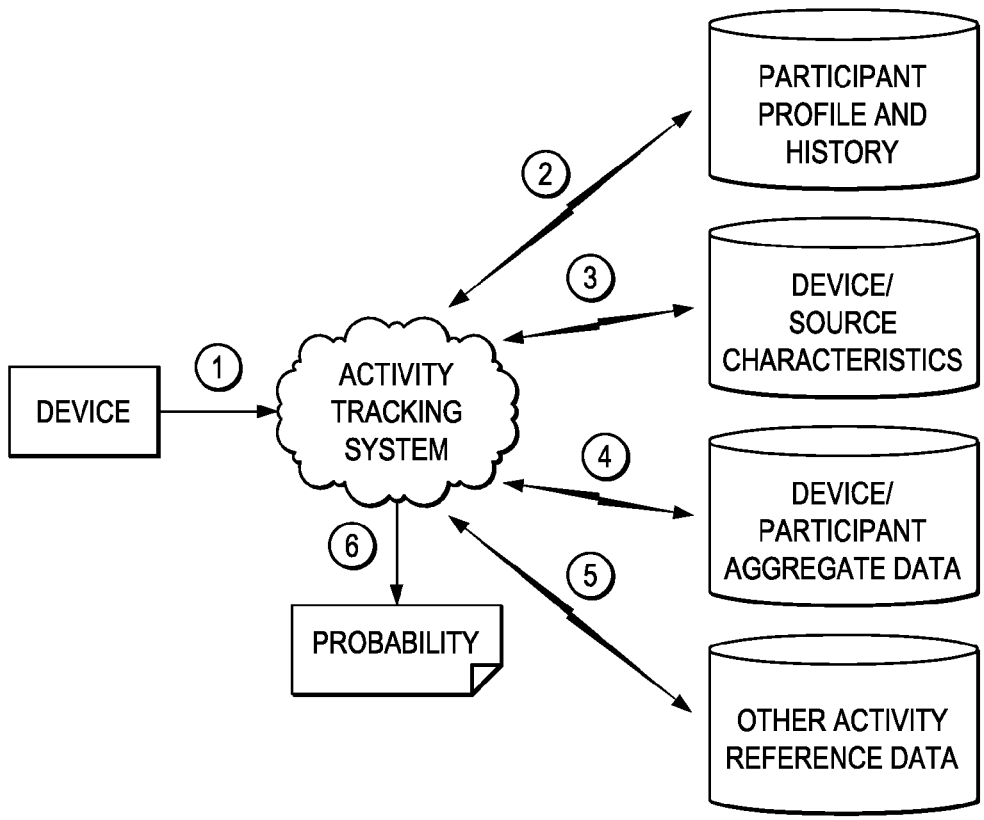
FIG. 4 illustrates a first embodiment of a method for verified workout wherein a device reports activity to the activity tracking system.

FIG. 4 illustrates a device-reported activity in a representative embodiment.

At step (1), the device reports an activity to the activity tracking system. The report may come from the device directly or indirectly (e.g., via an intermediary, a proxy, or the like). At step (2), the activity tracking system fetches any available information about the participant's history (e.g., one or more prior activity reports) or profile (e.g., the participant's height, weight, gender, age, or the like), as well as available type of time-series tracks available for the participant. At step (3), the activity tracking system fetches any available information about the device or source. This data may include, without limitation, device make and model number, known accuracy data, and the like. At step (4), the activity tracking system fetches any aggregate information about participants or devices that may be or are similar in some way to the report (e.g., other participants with a similar profile had similar activity reports) including any type of time-series tracks available for similar participants or activity reports. At step (5), the activity tracking system fetches other reference data about the activity (e.g., the elevation profile of the reported route). Steps (2)-(5) may be carried out concurrently, using known technologies, application programming interfaces, tools, protocols and transport mechanisms. One or more of such steps may be carried out asynchronously with respect to the device activity report, or in response to that activity report.

At step (6), the activity tracking system applies a probability matching algorithm to the data and information fetched (or some portion thereof) to generate a probability score. The probability score represents on the "likelihood" that the activity was actually completed by the participant. The score may be a numerical metric, a text value, or some combination thereof. A confidence level may be associated with the value.

At step (7), the activity tracking system publishes a probability report for this activity or participant. The report may be specific to the individual, or include the information in an aggregate value (for multiple participants). The report may be time-specific or include data over a time period. It is output to permitted users, systems or entities.

Figure 5:
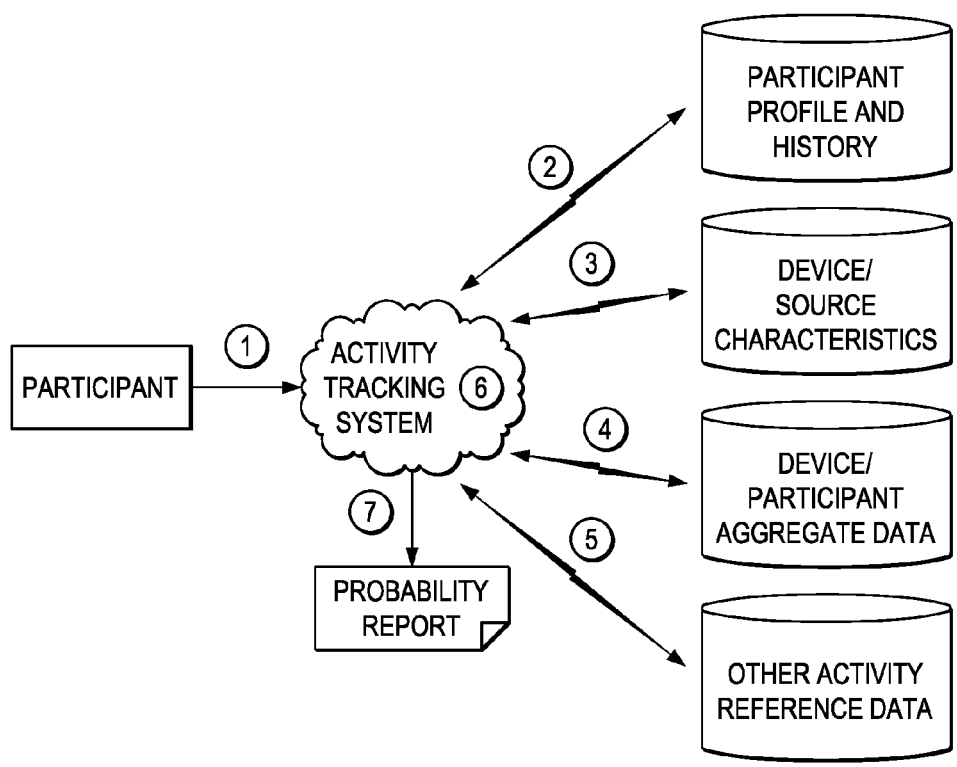
FIG. 5 illustrates a second embodiment of a method for verified workout wherein a participant reports activity to the activity tracking system.

FIG. 5 illustrates a participant-reported activity.

At step (1), the participant reports an activity to the activity tracking system. As described above, the report may come from the participant directly or indirectly (e.g., via an intermediary, a proxy, or the like). At step (2), the activity tracking system fetches any available information about the participant's history (e.g., one or more prior activity reports) or profile (e.g., the participant's height, weight, gender, age, or the like), as well as available type of time-series tracks available for the participant. At step (3), the activity tracking system fetches any available information about the device or source. At step (4), the activity tracking system fetches any aggregate information about participants or devices that may be or are similar in some way to the report (e.g., other participants with a similar profile had similar activity reports) including any type of time-series tracks available for similar participants or activity reports. At step (5), the activity tracking system fetches other reference data about the activity (e.g., the elevation profile of the reported route). Steps (2)-(5) may be carried out concurrently, using known technologies, application programming interfaces, tools, protocols and transport mechanisms. As noted in the previous example, one or more of such steps may be carried out asynchronously with respect to the device activity report, or in response to that activity report. At step (6), the activity tracking system applies a probability matching algorithm to the data and information fetched (or some portion thereof) to generate a probability score. The probability score represents on the "likelihood" that the activity was actually completed by the participant. At step (7), the activity tracking system publishes a probability report for this activity or participant.

Figure 6:
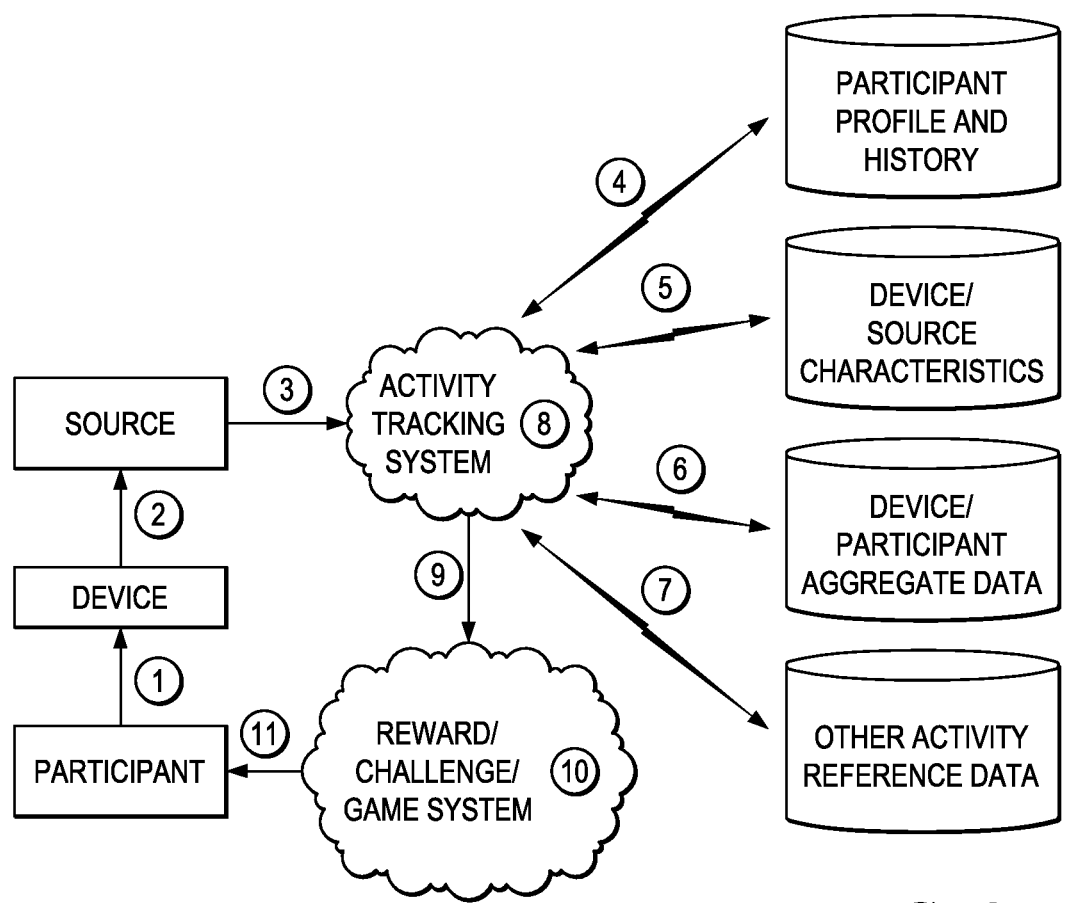
FIG. 6 illustrates how the disclosed verified workouts technique may be used in a reward/challenge/game system environment wherein verification results in an incentive being provided to or otherwise allocated to the participant whose workout has been verified.

FIG. 6 illustrates an alternative embodiment wherein the activity tracking system interacts with a system (which may be a third party system, web site or the like) that provides rewards, challenges or games, and wherein those types of incentives may depend on verifying a fitness activity according to the techniques that have been described herein.

At step (1), a participant uses a device to record an activity. At step (2), the device reports the activity, typically into an intermediary system or source. At step (3), the source reports the activity in the activity tracking system. At step (4), the activity tracking system fetches any available information about the participant's history (e.g., one or more prior activity reports) or profile (e.g., the participant's height, weight, gender, age, or the like), as well as available type of time-series tracks available for the participant. At step (5), the activity tracking system fetches any available information about the device or source. At step (6), the activity tracking system fetches any aggregate information about participants or devices that may be or are similar in some way to the report (e.g., other participants with a similar profile had similar activity reports) including any type of time-series tracks available for similar participants or activity reports. At step (7), the activity tracking system fetches other reference data about the activity (e.g., the elevation profile of the reported route). Steps (4)-(7) may be carried out concurrently, using known technologies, application programming interfaces, tools, protocols and transport mechanisms. As noted in the previous example, one or more of such steps may be carried out asynchronously with respect to the device activity report, or in response to that activity report. At step (8), the activity tracking system applies a probability matching algorithm to the data and information fetched (or some portion thereof) to generate a probability score. The probability score represents on the "likelihood" that the activity was actually completed by the participant. At step (9), the activity tracking system publishes the probability score to the reward/challenge/game system. At step (10), the reward/challenge/game system determines if an award is granted based on the reported activity and the probability score. If so, at step (11), the reward/challenge/game system provisions some benefit to the participant. That system may also aggregate multiple reports over time.

Any scoring algorithm (and associated verification metrics) may be used to determine whether an activity report can be verified against the data obtained by the activity tracking system. The following example provides a representative probability score calculation. A given number of baseline points (e.g., 10) are assigned for the submitted activity. The algorithm then checks to determine how many activities this particular participant has submitted previously. The scoring algorithm might then add, say, three (3) points if the user has submitted greater than, say, thirty (30) activities previously, but only one (1) point if the user has submitted greater than, say, then (10) activities previously. The scoring algorithm may subtract one (1) point if this is the first activity submitted by the user. After these weightings are assigned by the scoring algorithm, the scoring algorithm may then determine whether any one of the following metrics fit within a standard deviation of a given number (e.g., 10) of prior workouts by the user: kCals burned, duration, distance, average speed or pace, elevation, and the like. The scoring algorithm might also be set up to subtract, say, 0.5 points for each such metric that falls outside one standard deviation of the given number of prior workouts. The scoring algorithm may then check other data and assign points (or subtract them) appropriately. Thus, the algorithm may check to determine whether the participant's maximum (or average) speed for the activity falls outside one standard deviation for all users in the prior 12 months who fit a similar demographic and body mass index provided doing the particular activity (e.g., cycling); if so, the scoring algorithm subtracts one (1) point. The scoring algorithm may also check whether there is a GPS time-series track (e.g., latitude, longitude, accuracy, timestamp) for this workout; if so, the algorithm may then add several points. If the average accuracy of points for the GPS time-series is under a certain distance, another point may be added. If the distance of the activity falls outside one standard deviation for all users in the prior 12 months who fit a similar demographic and body mass index profile doing this activity, the scoring algorithm may then subtract another point, and so on, for other such determinations.

Of course, the above-described scoring algorithm is merely representative. Any one or more of such scoring criteria may be defined and applied, in any manner. The criteria may be applied concurrently, or sequentially. One or more mathematical functions may be applied to given scoring criteria. Once the score has been generated in this manner, it is compared to one or more predetermined thresholds for the scoring algorithm. In the event the scoring algorithm includes just one threshold (e.g., valid, or not valid), if the generated score exceeds the threshold, the probability value is output as valid. In the event the scoring algorithm includes multiple thresholds (e.g., valid, indeterminate, not valid), the probability value output will depend on where in the range the final score lies. Of course, any number of thresholds may be implemented by the scoring algorithm.

Scoring algorithms may be generated by a service provider or a third party, such as a third party contest provider.

Data used by the scoring algorithm is obtained from one or more of the data sources described above. The data may be obtained "on-the-fly" at the time the algorithm is executed, or in advance. Third party data sources (e.g., Internet databases, search engines, and the like) may be examined as well to obtain relevant data.

A participant may be queried by the activity tracking system during the process of executing the scoring algorithm.

A device or participant, or a database, may interact with the activity tracking system securely, and/or using conventional authorization and authentication techniques.

Preferably, a participant registers to the activity tracking system using a registration process, page or application module. During registration, the system builds and maintains a participant profile.

There are many potential use cases for the techniques described herein. They include one or more of the following, which are merely representative.

Health & Fitness Challenges have become a popular way to motivate participants to become more active by engaging in fitness-related activities such as running or riding a bicycle. In some cases, these challenges may have highly motivating prizes or rewards associated with them, causing an incentive for a participant to knowingly or accidentally submit an inaccurate or inauthentic activity report. Doctors and physical trainers often create physical or nutritional activity plans for participants. As participants complete the prescribed plan, they may create activity reports from various devices and sources. Understanding the likely authenticity of the report would aid the doctor or trainer in helping the participant achieve the desired outcome. In another scenario, a participant may be using a device or other source to track activities. Knowing the likelihood that the report was accurate is helpful to the participant. For example, if a participant used a GPS device to measure his or her bicycle ride, and the device reported that the ride was 30 miles, the participant would benefit from knowing the likely accuracy of this report for the purposes of managing his or her own training.

These examples should not be taken by way of limitation. This system has a broad range of application including health/fitness related contests and challenges, personal coaching, medical care and personal health records, and health insurance programs. These are merely exemplary use cases.

While the above describes a particular order of operations performed by certain embodiments of the invention, it should be understood that such order is exemplary, as alternative embodiments may perform the operations in a different order, combine certain operations, overlap certain operations, or the like. References in the specification to a given embodiment indicate that the embodiment described may include a particular feature, structure, or characteristic, but every embodiment may not necessarily include the particular feature.

While given components of the system have been described separately, one of ordinary skill will appreciate that some of the functions may be combined or shared in given instructions, program sequences, code portions, and the like.

As described above, the techniques described herein are provided using a set of one or more computing-related entities (systems, machines, processes, programs, libraries, functions, or the like) that together facilitate or provide the described functionality described above. In a typical implementation, the activity tracking system comprises one or more computers. A representative machine comprises commodity hardware, an operating system, an application runtime environment, and a set of applications or processes and associated data, that provide the functionality of a given system or subsystem. As described, the functionality may be implemented in a standalone node, or across a distributed set of machines.

The integrity verification techniques described herein need not be implemented using any particular delivery mechanism (e.g., over the Internet, using a client-server approach, or the like), or even practiced over a network. The technique also may be used in an off-line application, in the firmware or software of a non-connected device, or in any other computing environment.

The activity report whose integrity is verified according to the techniques described herein may describe other activity, such as biometrics (e.g., a user reports weight, and the technique reviews prior weight readings, etc. and assigns a score regarding the current report), nutrition (e.g., a user reports eating only 1500 Kcals in a day, and the technique reviews nutrition, weight activity history, etc. and assigns a score regarding the current report), or the like. Thus, as used herein, "fitness-related activity" should be broadly construed to cover these additional applications.

Having described our invention, what we now claimed is as follows.

The invention claimed is:

1. A method for verifying integrity of a fitness-related activity, comprising:
   receiving, by an activity tracking system running on one or more server machines, an activity report associated with at least one fitness-related activity that is reported to have been completed by a participant, the activity report including at least some information provided by a device associated with the participant and the fitness-related activity;
   the activity tracking system obtaining data comprising any available information about the participant's history or profile, any available information about the device or a source of the activity report, any aggregate information about participants or devices associated with other activity reports having a degree of similarity to the activity report, and reference data about the fitness-related activity; and
   the activity tracking system applying a probability matching algorithm to the data or a portion thereof to generate a probability score that represents a likelihood that the fitness-related activity was actually performed by the participant, the probability matching algorithm comprising a function for determining whether a metric of the fitness-related activity completed by the participant falls outside of one standard deviation for all users who fit a similar demographic and body mass index profile performing the fitness-related activity.

2. The method as described in claim 1 further including quantifying the probability and providing a value representing the quantified probability.

3. The method as described in claim 1 wherein the activity report is received from the device or the participant.

4. The method as described in claim 1 wherein the device is a mobile device, a pedometer, a GPS watch, a bio-monitor device, or a scale.

5. The method as described in claim 1 wherein the data includes at least one time-series track of data, wherein a time-series track of data represents a sequence of measurements over a time period.

6. The method as described in claim 1 further including providing an incentive based on the probability determination.

7. The method as described in claim 6 wherein the incentive is an award.

8. The method as described in claim 1 wherein the source of the activity report is the device associated with the participant, the participant, or a third party human or non-human entity.

9. The method as described in claim 1 wherein the activity tracking system at least partially provides or is provided by software-as-a-service (SaaS).

10. Apparatus, comprising:
one or more processors; and
an activity tracking system embodied on a computer memory holding computer program instructions executed by the one or more processors to provide a method for verifying workout data, the method comprising:
receiving an activity report associated with at least one fitness-related activity that is reported to have been completed by a participant, the activity report including at least some information provided by a device associated with the participant and the fitness-related activity;
obtaining data comprising any available information about the participant's history or profile, any available information about the device or a source of the activity report, any aggregate information about participants or devices associated with other activity reports having a degree of similarity to the activity report, and reference data about the fitness-related activity; and
applying a probability matching algorithm to the data or a portion thereof to generate a probability score that represents a likelihood that the fitness-related activity was actually performed by the participant, the probability matching algorithm comprising a function for determining whether a metric of the fitness-related activity completed by the participant falls outside of one standard deviation for all users who fit a similar demographic and body mass index profile performing the fitness-related activity.

11. The apparatus as described in claim 10 wherein the method further includes quantifying the probability and providing a value representing the quantified probability.

12. The apparatus as described in claim 10 wherein the activity report is received from the device or the participant.

13. The apparatus as described in claim 10 wherein the device is a mobile device, a pedometer, a GPS watch, a bio-monitor device, or a scale.

14. The apparatus as described in claim 10 wherein the data includes at least one time-series track of data, wherein a time-series track of data represents a sequence of measurements over a time period.

15. The apparatus as described in claim 10 wherein the method further includes providing an incentive based on the probability determination.

16. A computer program product in a non-transitory computer-readable medium for verified workouts, comprising:
a first software component associated with and executed by a device having a hardware element, the first component generating an activity report associated with at least one fitness-related activity that is reported to have been completed by a participant; and
a second component associated with an activity tracking system, the activity tracking system receiving the activity report generated by the first component, obtaining data comprising any available information about the participant's history or profile, any available information about the device or a source of the activity report, any aggregate information about participants or devices associated with other activity reports having a degree of similarity to the activity report, and reference data about the fitness-related activity, and determining a probability that the activity report represents fitness-related activity actually performed by the participant by applying a probability matching algorithm to the data or a portion thereof to generate a probability score that represents a likelihood that the fitness-related activity was actually performed by the participant, the probability matching algorithm comprising a function for determining whether a metric of the fitness-related activity completed by the participant falls outside of one standard deviation for all users who fit a similar demographic and body mass index profile performing the fitness-related activity.

17. The computer program product as described in claim 16 wherein the activity tracking system at least partially provides or is provided by software-as-a-service (SaaS).

18. The method as described in claim 1 wherein the aggregate information includes data for a configurable number of other users performing the fitness-related activity over a configurable prior time period and who fit a configurable profile to that of the participant.

19. The apparatus as described in claim 10 wherein the aggregate information includes data for a configurable number of other users performing the fitness-related activity over a configurable prior time period and who fit a configurable profile to that of the participant.

20. The computer program product as described in claim 16 wherein the aggregate information includes data for a configurable number of other users performing the fitness-related activity over a configurable prior time period and who fit a configurable profile to that of the participant.

* * * * *